(12) United States Patent
Krause et al.

(10) Patent No.: US 8,072,607 B2
(45) Date of Patent: Dec. 6, 2011

(54) MEASURING DEVICE FOR MEASURING OPTICAL PROPERTIES OF TRANSPARENT SUBSTRATES

(75) Inventors: Jochen Krause, Dresden (DE); Holger Proehl, Dresden (DE)

(73) Assignee: Von Ardenne Anlagentechnik GmbH, Dresden (DE)

( * ) Notice: Subject to any disclaimer, the term of this patent is extended or adjusted under 35 U.S.C. 154(b) by 152 days.

(21) Appl. No.: 12/297,893

(22) PCT Filed: Oct. 30, 2007

(86) PCT No.: PCT/DE2007/001951
§ 371 (c)(1),
(2), (4) Date: Mar. 24, 2009

(87) PCT Pub. No.: WO2008/052526
PCT Pub. Date: May 8, 2008

(65) Prior Publication Data
US 2011/0007320 A1    Jan. 13, 2011

(30) Foreign Application Priority Data
Oct. 30, 2006    (DE) .......................... 10 2006 051 717

(51) Int. Cl.
*G01N 21/47* (2006.01)
(52) U.S. Cl. ......... 356/446; 356/432; 356/236; 250/228
(58) Field of Classification Search .................. 356/446
See application file for complete search history.

(56) References Cited

U.S. PATENT DOCUMENTS

| | | | |
|---|---|---|---|
| 4,597,665 A * | 7/1986 | Galbraith et al. | 356/239.8 |
| 4,655,225 A * | 4/1987 | Dahne et al. | 600/316 |
| 4,660,984 A * | 4/1987 | MacDonald | 356/446 |
| 4,744,615 A | 5/1988 | Fan et al. | |
| 5,164,586 A | 11/1992 | Hohberg et al. | |
| 5,184,013 A * | 2/1993 | Boutet et al. | 250/236 |
| 2002/0018203 A1 | 2/2002 | Battle et al. | |
| 2002/0089700 A1 * | 7/2002 | Mead | 358/302 |
| 2008/0285060 A1 | 11/2008 | Zoller et al. | |

FOREIGN PATENT DOCUMENTS

| | | |
|---|---|---|
| DE | 102005010681 A1 | 9/2006 |
| EP | 0458223 A2 | 11/1991 |
| GB | 2147413 A | 5/1985 |

OTHER PUBLICATIONS

The International Search Report for PCT/DE2007/001951, dated Feb. 26, 2008.

* cited by examiner

*Primary Examiner* — Gregory J Toatley
*Assistant Examiner* — Rebecca C Slomski
(74) *Attorney, Agent, or Firm* — Heslin Rothenberg Farley & Mesiti P.C.

(57) ABSTRACT

A measuring device for measuring optical properties of transparent substrates includes a light transmitter and/or light receiver comprising a hollow cylinder having a highly reflective and diffusely dispersive inner surface. The light transmitter comprises a light source arranged in its interior and a light exit opening at a distance from the light source. The light receiver has a light sensor instead of the light source, at a distance from a light entrance opening. The light source and light sensor are arranged at such a distance from the light exit opening and light entrance opening respectively, given a corresponding direction of propagation of the light, that light emitted by the light source or received by the light sensor and multiply reflected in the hollow cylinder emerges as diffuse light from the light exit opening or is incident on the light sensor.

23 Claims, 4 Drawing Sheets

MEASURING DEVICE FOR MEASURING OPTICAL PROPERTIES OF TRANSPARENT SUBSTRATES

CROSS REFERENCE TO RELATED APPLICATIONS

Figure 1:
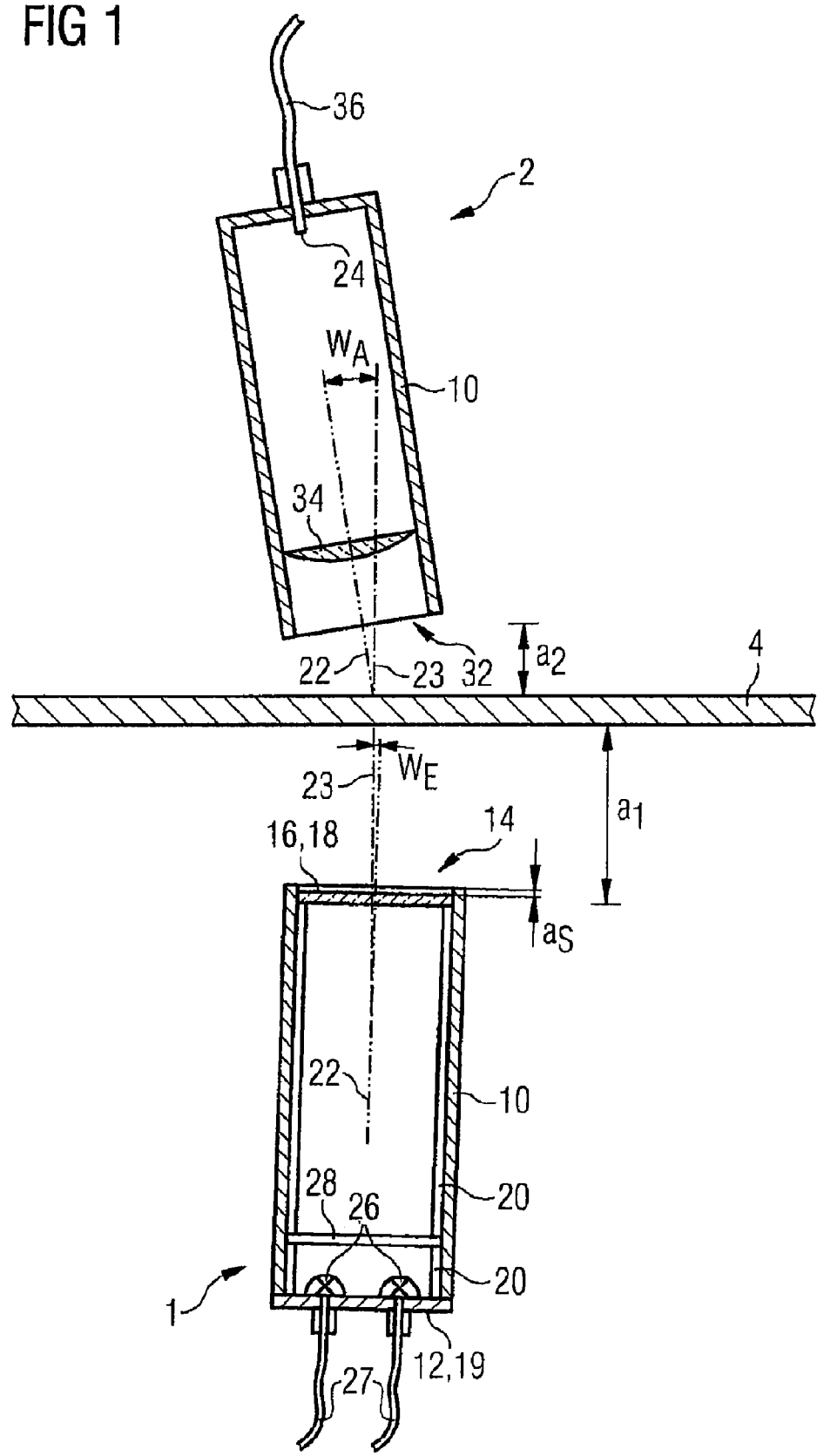

This application is a national stage filing under section 371 of International Application No. PCT/DE2007/001951, filed on Oct. 30, 2007, and published in German on May 8, 2008 as WO 2008/052526 and claims priority of German application No. 10 2006 051 717.2 filed on Oct. 30, 2006, the entire disclosure of these applications being hereby incorporated herein by reference.

BACKGROUND ART

The invention relates to a light transmitter, a light receiver and a measuring device with the use of such a light transmitter or light receiver for measuring optical properties of transparent substrates.

There are light transmitters or light receivers comprising a hollow body having a highly reflecting and diffusely dispersive, i.e. white, inner surface, a light source and/or light sensor arranged inside the hollow body and light exit opening and a light entrance opening at a distance therefrom. Apart from the light transmitter, which emits diffuse light for illuminating the substrate to be measured, the measuring device largely comprises a light receiver, which is arranged in the optical path of the light, which is emitted from the light transmitter and has passed through the substrate or has been reflected by the substrate.

Usually, collimated radiographic light is aligned on the sample for measuring the transmission and reflection properties of various transparent media like glass, films, coatings or glass filters. Subsequently, the light passing through is once again displayed in an optical characteristic and analyzed in accordance with the measuring task.

This measurement geometry fails to work in the case of concave objects like spectacle lenses, coated lenses or in the case of dispersive, randomly deflective substrates i.e. radiation without intensity loss, like diffusion disks for signal systems. Here, as also in the case of cloudy liquids, it is necessary to measure with diffuse light. In this case, the requirements are extremely customized and depend on properties of the objects. The design generally comprises a light source, arranged in an integration sphere or integrating sphere with its exit opening facing a light receiver that absorbs the emerging light. Likewise, it is also possible to collimate the optical path of a light source and align it on the sample opening of the integrating sphere. In both the arrangements, the device to be measured is introduced in the optical path close to the sphere opening.

An integration sphere or integrating sphere is a hollow sphere having an inner surface with absolutely matte reflection properties. The light of a light source arranged inside the sphere is multiply reflected so that each surface section of the interior surface as well as an exit opening is illuminated equally brightly and its luminous density is proportional to the total luminous flux.

Depending on the direction of the optical path, the substrate along with its surface section to be measured positioned directly at the exit opening or incidence opening of the integration sphere is either diffusely illuminated, i.e. penetrating from a number of various directions or the light dispersed in the substrate is completely absorbed with the sphere. According to each of the selected measurement geometries, a light receiver or a light transmitter is arranged across the substrate facing the exit or incidence opening of the sphere with a defined angular orientation.

E.g. description of a measuring device is given in EP 0 458 223 A2, which uses an integrating sphere as a light receiver for measuring absorption of transparent samples with irregularly arranged surfaces. The samples to be measured are arranged in the integrating sphere automatically or in a volume linked with the sphere, whose surface indicates the same multiply dispersive properties like the inner surface of the sphere. However, such an arrangement is suitable only for small sample geometries.

During the manufacture and/or quality control of optical products, it is often necessary to determine their optical properties for e.g. the reflection and transmission characteristics, and monitor in-situ in order to control the manufacturing process. This is especially the case, if, in a coating process, thin coatings with great uniformity, defined coating thickness and defined optical properties are to be applied on laminar substrates.

For instance, as the angle-dependent transmission of substrates is modified by applying thinner, sputtered coatings for instance, the coating growth is to be observed and controlled from the point of view of quality and thickness by means of the in-situ measurement of transmission during the manufacturing process. The dispersion in the thin coatings itself is in this case insignificant.

In order to measure the reflection and transmission of the coated substrate, photometers are used in the coating chamber, for instance, for the viability of short optical paths, which capture the monochromatic transmission and/or reflection signal of the substrate and a reference signal of the light source of the photometer.

The measuring device described in DE 10 2005 010 681 A1 is suitable for plasma or ion beam-aided processes, where the optical path is clearly extended on account of the significantly great distance of the coating, ion or plasma source from the substrate and on account of the protection required by the measuring device against spurious material deposits. Even in this device, the substrate to be measured intersects the optical path between a light source and a light receiving unit and in any case, there exist high standards in the adjustment of the light transmitter in particular. The protection of the measuring device against the coating source takes place in the last-mentioned device by means of a diaphragm.

A measuring device for the measurement of transmission and reflection for the purpose of the quality control of tape-like paper is described in GB 2 147 413 A. An integrating sphere for measuring the reflected light and light emitted through the substrate is arranged above and below the substrate.

However, the use of an integration sphere as a light transmitter or light receiver for measuring dispersive substrates, for instance, is advantageous neither for measuring in a coating chamber nor for the in-situ measurement of a continuous manufacturing process on account of the susceptibility of such a measuring arrangement to damage and its high costs. Furthermore, in the case of thicker substrates with a high degree of transmission and two reflecting surfaces, the face-to-face arrangement of the light receiver and light transmitter leads to the falsification of the measurement results due to the parts entering into the light receiver, which would be repeatedly reflected between the substrate surfaces.

BRIEF SUMMARY OF INVENTION

The invention aims therefore to specify a device for measuring optical properties of transparent substrates, which can also be used for in-situ measurement in vacuum coating equipments and measurement of dispersive substrates, avoids a falsification of the measurement in such substrates through multiple reflections in the substrate and at the same time enables a low instrumental and cost expenditure.

With the described light transmitter and light receiver as a significant part of the measuring device for measuring optical properties of transparent substrates, it is also possible to align diffuse light on the substrate and absorb diffuse light on the spot size, comparable to the integration sphere. The design of the light transmitter and the light receiver as a hollow cylinder is considerably easier and cost-effective to manufacture and likewise easier to maintain as compared to the integration sphere. The described light transmitter and light receiver are thus suitable especially for use under special climatic, measuring conditions and in coating equipments. It is also possible to use several light transmitters or light receivers for measuring a substrate. As the described device can be used for coated as well as uncoated substrates; hereinafter, the discourse should generally be about substrates, irrespective of whether or not they are coated.

The light emitted from the light source of a light transmitter in the hollow cylinder is multiply reflected against the highly and diffusely reflective inner surface, so that the light emitted through the light exit opening of the hollow cylinder exhibits a directional distribution of the intensity of radiation, which, compared to radiation emitted from an integration sphere exhibits a characteristic club shape with an intensity that is proportional to the respective angle of the cosine. The angle considered here is the one between the optical axis of the light transmitter and the direction of propagation of light considered in each case.

As the light exit opening is located in one of the bases of the hollow cylinder, only radiation with an angle between 0° and a maximum value of less than 90° is included in the directional distribution. This maximum value is exclusively accounted for geometrically by the diameter of the hollow cylinder in proportion with the dimensions and position of the light exit opening and leads to a club shape, which is slender, i.e. exhibits a lower angle of aperture than in the case of an integration sphere. However, this only has a negligible influence on the transmission measurement, as the part of the missing direction of propagation can be minimized on the one hand, by the geometrical embodiment of the light transmitter and on the other hand, by its positioning with a defined distance from the substrate. Furthermore, this effect is minimized especially during the measurement of marginally dispersive substrates, since it has been determined that the radiation, which reaches the substrate with a large angle, does not enter a light receiver through the substrate on account of their dispersion in the substrate, as the light receiver is positioned towards the substrate with a minor angle.

A minimum length of the hollow cylinder is necessary in order to reach the characteristic intensity distribution with the help of the light transmitter. This must be measured in such a manner that an adequate number of reflections can take place so that there is need to determine the preferred direction of light. In order to measure, it is also necessary to consider the intensity distribution of the selected light source and its position vis-à-vis the light exit opening.

The aspects with respect to the design and the functioning of a light transmitter described above similarly also apply to a light receiver, which comprises a light sensor for the absorption of light incident and diffusely reflected in the light receiver instead of a light source. The light entering into the light entrance opening is multiply reflected on the highly and diffusely reflective inner surface of the hollow cylinder of the light source, so that the light emerging on that base of the hollow cylinder, which is facing the light entrance opening and in which the light sensor is arranged, exhibits the directional distribution of the intensity of radiation described above. Even in the case of a light receiver, the relevant angle is the one between the optical axis of the light receiver and the direction of propagation of light considered in each case.

To optimize the length of the hollow cylinder and absolutely make sure that a diffuse reflection of light incident in the hollow cylinder takes place for instance in the case of slightly dispersive substrates, according to an embodiment of the light transmitter or light receiver, the light exit and/or light entrance opening is completely covered with a transparent, light dispersing plate, hereinafter referred to as diffusion disk. The light multiply reflected in the hollow cylinder and/or incident on the light entrance opening is dispersed with the diffusion disk. For a light transmitter, the light emitted from the latter is radiated in almost all directions and thus fulfils the requirements of a transmitter emitting diffuse light for measuring transmission especially in dispersive substrates.

In the case of a light receiver, it is also possible to measure slightly dispersive substrates and even independent of the use of the light transmitter by using a diffusion disk, as in no way can a direct optical path result from the light transmitter through the substrate or through reflection on the substrate to the light sensor. As the intensity of the absorbed radiation or its transformation into a defined spot size is measured and analyzed, comparable to the measurement with an integration sphere, for measuring the optical properties of the radiated or reflective substrate, so that a direct, i.e. diffusely reflected optical path does not falsify or even prevent the measurement.

Furthermore, the effect of the diffusion disk can be influenced by a suitable choice or modification of the material used for the diffusion disk in a targeted manner. In the simplest case, at least one diffusion disk can be an evenly sandblasted glass or plastic disk. A holographic diffuser or a diffuser with micro-lenses or micro-wedges can also be used.

Likewise, for a major dispersion effect it is possible to arrange a second diffusion disk in the hollow cylinder parallel to and at a distance from the first diffusion disk in such a manner that the light in the hollow cylinder also passes through the second diffusion disk. In this manner, the effect can be multiplied through multiple reflections on the inner surface of the hollow cylinder by using a diffusion disk. Special effects can also be achieved in the reflection through the appropriate choice of the inner lateral area of the hollow cylinder above the first diffusion disk, i.e. after the passage of light through the first level, whereby special application-specific requirements can be corresponded to the measurement. Similarly, it is possible to choose material combinations for the diffusion disks.

A favorable intensity distribution with a large maximum value of the emergent angle of light emitted from the light exit opening of a light transmitter or entering into the light entrance opening of a light receiver is achieved if, according to another embodiment of the light transmitter, the respective opening exhibits the dimensions of the surface of the interior surface of the hollow cylinder facing the opening, i.e. the opening of the hollow cylinder for the entry or exit of light is not reduced with respect to the internal diameter of the hollow cylinder, light entry or exit are not restricted by diaphragms or the like.

Furthermore, it also has a favorable impact for an even intensity distribution on account of even multiple reflections in the hollow cylinder, if the light source is arranged in the second base facing the first base. It is understood that the light source or light sensor can alternatively also be arranged in another surface of the hollow cylinder, e.g. in order to rule out a direct optical path of light between the opening and light source and/or light sensor even in the case of a missing diffusion disk.

The described light transmitter and light receiver are very flexible in design. By adding various components, they can be easily adapted to the measuring task by the user himself e.g. with respect to the light source and/or light sensor, the spectrum or polarization. It is designed in such a way that its embodiment as a hollow cylinder can easily adjust the light emitted from the light source and absorbed by the light sensor to specific requirements by using filters, by arranging the filter(s) in the hollow cylinder in such a manner that the light passing through the hollow cylinder also necessarily passes through each filter. Disk-shaped filters, fitted in the cylinder consecutively with a defined distance, parallel to the first base are appropriate for this purpose. In the case of the arrangement of several filters, the distance between the filters and the distance from the light source and/or the light sensor as well as from the opening of the hollow cylinder is to be selected in such a way that it does not interfere with satisfactory multiple reflections.

Polarization filters or colored filters for instance can be used. Polarization filters are, for instance, used for specific materials of the substrates to be measured or in the case of specific coating materials deposited on a carrier material. On the other hand, colored filters especially affect the spectral adjustment of light from the light source, e.g. to the configuration of the light receiver in order to improve the modulation. Other filters are also used depending on the optical properties of the substrate, light source or light sensor to be measured.

Different embodiments can be used as light sources depending on the required intensity of the spectrum, climatic conditions of use or the measuring task. For measuring the coating thickness of the metallic coatings deposited on a carrier material, e.g. an infrared source can be used whereas a white light source is used e.g. for the determination of the transmission spectrum of dielectrical coatings. In this case, the light receiver comprises a polychromator used to split and evaluate the absorbed light into its spectral parts.

Furthermore, light sources can either be in the radiation source arranged in the hollow cylinder, such as laser or discharge lamps, or even light conducting, projecting or reproducing optical arrangements such as fiber glass, object lenses, refractors, mirrors or integrated optical wave guides or even optical components such as LEDs emitting optical light. Halogen lamps, deuterium lamps or xenon lamps are used as light sources with a wide spectrum and high luminous density by way of example. Or the light exit opening of a projecting luminous fiber optic light guide serves as a light source in the hollow cylinder. The latter works such that the thermal impact of the hollow cylinder and with it a thermal effect negatively affecting the emission spectrum of the light transmitter are avoided.

In another embodiment of the light transmitter, another light source is arranged in the hollow cylinder, which is located at a place comparable to the first light source, so that even light emitted from the second light source diffusely emerges at the light exit opening of the hollow cylinder. Therefore both light sources are regularly arranged directly next to each other. Although an undesired, locally contingent, thermal impact is associated therewith, it is still possible to arrange both light sources at a distance from each other.

Insofar as the second light source is to be operated independent of the first one, downtimes of a light source can be compensated or special measuring requirements can be fulfilled with a corresponding combination of both sources.

Similarly, the light sensor of the light receiver can also be adapted to the respective measuring task, the substrate and the properties of the light used. In the corresponding embodiment of the light receiver, known light sensors can be used, e.g. a photodiode, photo resistance or even the entry of a fiber optic light guide in addition to the described use as a light source combined with a collimator. In another embodiment, several grid-like light sensors arranged in a surface can also be used for increasing the spot size. The use of a fiber optic light guide as a light sensor allows fitting the detector outside the measuring setup and thus making it easily accessible for the operation or coupling it possibly directly with the evaluation unit. Such a design can be used e.g. for the in-situ measurement of optical properties of coatings to be deposited in a coating equipment.

If other embodiments of the light transmitters or light receivers are built in such a way that the white inner lateral surface of the hollow cylinder is formed with a hollow cylinder retractable into an outer hollow cylinder, the production of the hollow cylinder with that specific inner surface can take place especially in a cost-effective and flexible manner. This embodiment allows manufacturing e.g. the outer hollow cylinder made of a stable, adequately available material, e.g. steel or plastic and using the specific material with the required optical properties e.g. white polytetrafluoroethylene (PTFE) only for the inner hollow cylinder to be retracted without clearance.

Depending on the current measuring task, the modification of the light transmitter or light receiver is possible only if the inner hollow cylinder is subdivided into two or if necessary even more hollow cylindrical sections and a diffusion disk and/or a disk-shaped filter can be inserted between two hollow cylindrical sections. To this effect, the diameters of the disks to be added correspond to the internal diameter of the outer cylinder and thus to the outer cylinder of the inner cylinder. In this manner, the inner components of the hollow cylinder, such as diffusion disks and filters can be modularly varied by guiding individual hollow cylindrical sections and disks into the outer hollow cylinder in the corresponding sequence. The distance between the individual components can be produced with the height of individual or multiple hollow cylindrical sections joint to each other.

A measuring device measuring optical properties of the transparent substrates using the described light transmitter or light receiver or both the devices is essentially designed similarly to an integrating sphere, whereupon the described light transmitter as well as the described light receiver can be arranged at a distance from the substrate without appreciably affecting the measurement results. On account of this possible arrangement of the light transmitter and light receiver, the transmission as well as reflection or simultaneously both are to be measured with the measuring device.

On account of the characteristic, mace-shaped intensity distribution of the light reaching the surface section of the substrate to be measured from the light transmitter described above, the light transmitter can be arranged in a measuring device for the measurement of transmission with an angle, which equals approximately 0°. The angle, with which the light transmitter is arranged, is the angle between the optical axis of the hollow cylinder and the surface normal of the surface of the substrate against the light transmitter and is hereinafter referred to as the angle of incidence. Surface normal generally refers to such a line that is perpendicular to all the lines of the considered surfaces.

On account of the distance of the light transmitter from the substrate, the intensity distribution of light is similar to the distribution achieved with an integration sphere, so that the exact setting of a defined angle is then no longer necessary contrary to the known measuring device, which aligns collimated light on the substrate. This minimizes the effort to adjust the position and especially the angle of the light transmitter significantly and thus simplifies the manageability of the measuring device.

Thus, in the case of such an embodiment of the light transmitter, with which a broad club-shaped intensity distribution can be achieved, the angle of incidence can lie in the range of 0° to ±15°. An angle of incidence in the range of 0° to ±10° is especially preferred.

The described measuring device and the distance between the light transmitter and substrate in particular as well as the possibility of tipping the light transmitter facing the surface normal of the surface of the illuminated substrate section against the light transmitter also allows the light transmitter to be arranged with such an angle that another light receiver is arranged in the optical path of light emitted from the light transmitter and reflected from the substrate. This allows the simultaneous measurement of transmission and reflection in a measuring device.

The described measuring device also easily allows the implementation of standards for instrument geometries of optical measuring devices e.g. the CIE standard. The emergent angle thus equals close to 8° in the case of diffuse illumination of the sample in accordance with the Standard CIE Diffuse/8°. The application of this standard in the measuring device prevents the previously described falsification of the measurement results and at the same time measures up to the club shape of the intensity distribution of the light emitted from the light transmitter described above.

For measuring reflection as well, standard geometry can be implemented favorably because of the above-mentioned limitations of the angle of incidence to maximum ±15° likewise CIE Diffuse/8°. To this effect, the light transmitter with an angle of incidence of near 8° as well as the other light receiver mirrored on the surface normal are aligned with a comparable angle different from the angle of incidence, hereinafter referred to as angle of reflection, so that the other light receiver is still arranged in the optical path of the light reflected from the substrate.

Since all the measurements described here are based on the Lambert-Beerschen law, i.e. on quotient formation of light intensity I of the light penetrating through or reflected from the substrate and the intensity of the incident light $I_0$, a falsification of the measurement results may occur in the case of a perpendicular arrangement of a light receiver to the substrate surface due to that part of light, which penetrates the receiver between the substrate surface and the interface of the light receiver after multiple reflections. Thus, according to an embodiment of the measuring device, the light receiver is arranged in the optical path of the light passing through the substrate with an angle of greater than 0°, so that only the corresponding part of the angle is reproduced in the receiver. This angle is included from the direction of the part of light to be detected and the surface normal of the surface of the substrate against the light receiver. This angle is hereinafter referred to as the emergent angle.

BRIEF DESCRIPTION OF THE DRAWING FIGURES

For a better understanding, the invention is explained in detail below with the help of an execution example and a diagram. These show FIG. 1 a measuring device for measuring transmission using a light transmitter according to claim 1, FIG. 2 a measuring device for measuring transmission using a light receiver according to claim 2, FIG. 3 a measuring device for measuring transmission and reflection using a light transmitter and light receiver according to the invention and FIG. 4 a measuring device for measuring reflection using a light transmitter according to claim 1.

DETAILED DESCRIPTION

The measuring device represented in FIG. 1 comprises a light transmitter 1 according to claim 1, whose light exit opening 14 is aligned on a light receiver 2. The substrate 4 to be measured is located between the light transmitter 1 and light receiver 2, e.g. a glass substrate with light dispersing properties which is arranged at a first distance $a_1$ from the light transmitter 1 and at a second distance $a_2$ from the light receiver 2. In the execution example, the first distance $a_1$ is greater than the second distance $a_2$, which does not necessarily have to be the case. In an embodiment of the measuring device, not represented in detail, the light transmitter 1 can be arranged 1 with the end of the hollow cylinder 10 directly on the substrate 4, so that the hollow cylinder 10 and the substrate 4 remain in contact.

The light transmitter 1 used comprises an outer hollow cylinder 10, which is sealed on both the bases with a disk-shaped component. The length of the outer hollow cylinder 10 equals more than double its diameter. The first base 12 of the hollow cylinder 10 against the substrate 4 is sealed with a diffusion disk 18, designed in the execution example as sandblasted glass disk. The diffusion disk 18 is fitted in the outer cylinder 10 with positive locking. The surface of the diffusion disk 18 against the substrate 4 is arranged at a distance $a_s$ from the end of the hollow cylinder 10, which approximately corresponds to the thickness of the diffusion disk in the execution example but may also vary. On account of this distance $a_s$, there is a distance $a_s$ between the diffusion disk and the substrate 4 directly on the substrate 4 in the case of the arrangement of the hollow cylinder 10 described above.

The second base 16 of the hollow cylinder of the light transmitter 1 is sealed with a base plate 19, e.g. made of plastic. In the base plate 19, there are two light sources 26 flushed centrally and at a distance from each other, e.g. two halogen lamps, which radiate in the hollow cylinder and have a cable 27 guided outwards through a base plate 19.

A disk-shaped blue filter 28 is fitted parallel to the base plate 19 and at a distance from the light source 26. The blue filter 28 balances the yellowish spectrum of the halogen lamp to a certain extent and changes it to an even and smooth distribution through the existing range, so that the spectrum is adjusted better to the light receiver 2 used in order to achieve an even modulation.

The inner wall of the hollow cylinder of the light transmitter 1 is formed by two inner hollow cylindrical sections 20, the outer diameters of which correspond to the internal diameter of the outer hollow cylinder 10 in an almost equal measure. The first inner hollow cylindrical section 20 is added between the diffusion disk 18 and the blue filter 28 and thus defines the distance between the two components. It comprises white PTFE, which exhibits the high degree of reflection and the surface roughness required for generating diffusely dispersed light. Instead of the inner hollow cylinder, the inner surface 11 of the outer hollow cylinder 10 can alternatively be manufactured with similar optical properties (FIG. 2), e.g. wherein the hollow cylinder itself is made out of this or another suitable material with the indicated properties or whose inner surface is coated accordingly. In this case, an inner hollow cylinder or inner hollow cylindrical section 20 is omitted and suitable retaining means, not represented in detail, are provided in the interior of the outer hollow cylinder 10 for holding filters and diffusion disks.

The second inner hollow cylindrical section 20 of the described example is arranged between the base plate 19, which closes the outer hollow cylinder 10, and the blue filter 28. The length of the first hollow cylindrical section 20 equals a multiplicity of the length of the second hollow cylindrical section 20. Even the second hollow cylindrical section 20 comprises white PTFE, which does not necessarily have to be the case in the case of a possibly large proportion of the length of the second hollow cylindrical section 20 to the length of the first hollow cylindrical section 20.

The light transmitter 1 is aligned on the light receiver 2 in such a way that the axis of the outer hollow cylinder 10, which coincides with the axes of both inner hollow cylindrical sections 20, exhibits the same orientation as the surface normal of the illuminated section of the substrate surface. An accurate alignment on the orientation of the surface normal is not necessary, so that a deviation remains and an angle of incidence $W_E$ of approximately 1 degree is formed in the example.

One of the two light sources 26 is operated for illuminating the substrate 4. The light radiated from the active light source 26 and penetrating through the blue filter 28 already exhibits different directions of propagation and is multiply reflected in the first hollow cylindrical section 20, so that the light entering the diffusion disk 18 already exhibits a diffuse character and ensures the uniform illumination of the diffusion disk 18. Another dispersion takes place during the passage through the diffusion disk 18, which leads to a uniform illumination of the surface of the light entrance opening 32 of the light receiver 2, also referred to as receiver surface, and to the described characteristic intensity distribution.

To receive the light emitted from the light transmitter 1, the light receiver 2 as light sensor 24 exhibits the entrance of a fiber-optic light guide 36 with a collimator 34. The light receiver 2 as well comprises a hollow cylinder 10 that represents a light exit opening 32 to the base against the substrate 4. A collimator 34 is added in the hollow cylinder 10 at this end and at a distance from the end in order to change the angle of the light incident in the light entrance opening 32 in such a way that it is smaller than or equal to the acceptance angle of the fiber-optic light guide 36, through which the conduction of light takes place by means of total reflection. It is understood that different collimators 34 as well as differently designed light sensors 24 can be used based on the wave length of the light or of other optical parameters of the measuring device. E.g. Lens or diaphragm systems are known as collimators 34 and light sensors 24 on the basis of photodiodes.

The light receiver 2 is linked with a light detector unit not represented in detail, which comprises a polychromator. The measurement of transmission can thus be carried out on the entire wave length spectrum, which enables the measurement of the continuous change of optical properties as a result of the change in the thickness of the coating during the deposit of a thin coating on a carrier substrate in a vacuum plant. Alternatively, the light detector unit can also consist of a dispersive element, especially a monochromator, so that spectral photometric measurements are possible.

As is known, there is not just a single transmission value for the characterization of a material but dependence on the angle distribution of the incident intensity and on the angle range, in which the radiation emitted and passing through the substrate 4 is measured. On account of the last-mentioned dependence, the light receiver 2 is positioned in the optical path of the emitted light with a defined exit angle $W_A$, in the described example with an angle of 8° as per CIE Standards Diffuse/8°. Even the exit angle between the optical axis 22 of the light receiver 2 here and the surface normal 23 of the substrate surface 4 is measured. The symmetrical axis of the optical elements of the hollow cylinder of the light transmitter 1 or light receiver 2 here is referred to as optical axis 22. Normally, the surface normals 23 of both surfaces of the even substrates 4 are parallel to each other. However, as the measurement does not have to be limited to substrates 4 with parallel surfaces, each angle specification is based on the surface normals 23 of the illuminated surface of the substrate 4. The angle specifications are thus comparable with each other.

The evaluation of the transmission of a substrate 4 is based on the quotient formation from light intensity I of the light penetrating though the substrate 4 and the intensity of the incident light $I_0$. In order to determine the transmission of a substrate, the measured value determined with substrate 4 is set in proportion to the measured value, determined with a similar measuring arrangement without substrate 4 by taking the last value as the $100^{th}$ transmission. In order to determine and consider the noise level as a result of the residual light or some other impact on the light receiver, another measurement is carried out without substrate 4 and with covered light transmitter 1. The analysis of the measured values of the measuring, reference and blocked phases for the derivation of the angle-dependent transmission value takes place in a suitable processor unit, which has not been represented in detail.

Figure 2:
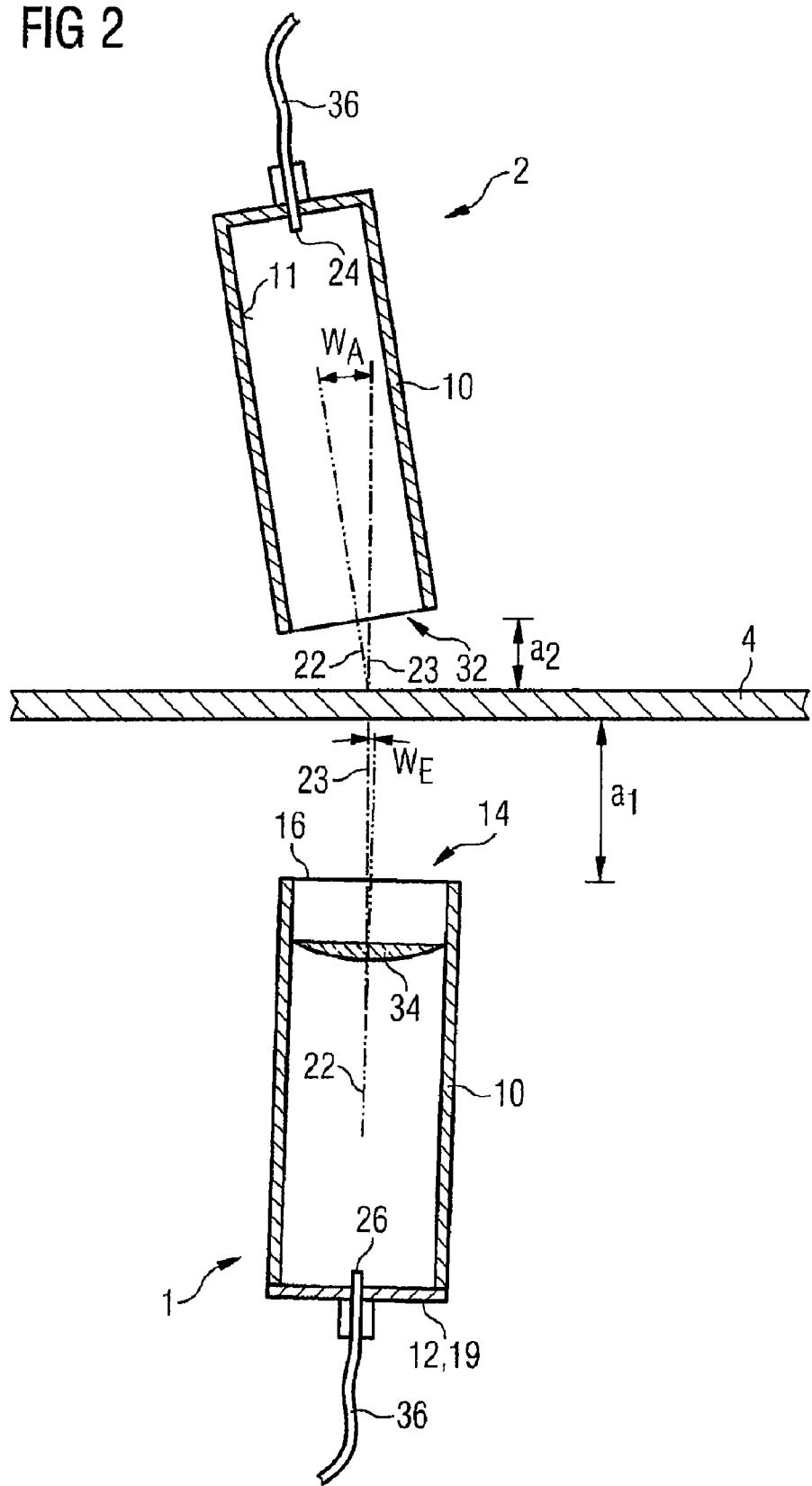

FIG. 2 shows a measuring device according to the invention using a light receiver 2 according to claim 2. A measuring device comprising such a light receiver 2 is to be modified in such a manner that a light transmitter 1 aligns collimated light on the light entrance opening 32 of the light receiver 2 and thus illuminates a substrate 4 positioned in front of the light entrance opening 32. The light transmitter 1 consists of a hollow cylinder 10, which has the output of a fiber-optic light guide 36 as light source 26 against the base plate 19 in its first base 12 turned away from the substrate 4. Light is generated with parallel beam path and is aligned on the substrate 4 using the collimator 34 arranged at the other end of the hollow cylinder 10 but at a distance from the end. Instead of such a light transmitter 1, a differently designed, conventional light transmitter 1 can be used in another embodiment, which emits collimated light on the substrate 4.

Even light transmitter 1 in FIG. 2 is, as described in FIG. 1, slightly inclined towards the surface normal 23 of the substrate 4 such that the angle of incidence $W_E$ equals approx. 1°. As described above, the inclination of the light transmitter 1 is based on a relatively greater tolerance as compared to well-known measuring devices. Consequently, other angles of inclination can also exist or the angle of incidence $W_E$ can equal 0°.

Light receiver 2 consists of a hollow cylinder 10 with a white inner surface 11, which is thus diffusely reflective. The measuring device represented in FIG. 2 serves in the measurement of dispersive properties of substrates 4 with light, so that the light emitted through the substrate 4 with such a dispersion is incident in the light entrance opening 32 of the light receiver 2, that no beam of light is incident directly on the light sensor 24 from the light source 26 and a diffuse reflection can take place in the hollow cylinder 10 of the light receiver 2. If this requirement is not met on account of the low dispersion effect of the substrate 4, the light receiver can alternatively also be complemented with a diffusion disk 18 in the hollow cylinder 10. Irrespective of the use of a diffusion disk 18, the light entrance opening 32 is to be dimensioned on the basis of the dispersion effect of the substrate 4 in such a manner and is to be positioned so closely on the substrate 4 that the total light emitted through the substrate 4 can be detected. The angular arrangement of the light receiver 2 likewise equals 8° in the execution example represented for the implementation of the CIE Standard Diffuse/8°.

The light incident on the spot size, represented in the embodiment of the entrance of a fiber-optic light guide 36, is transmitted for the analysis of an unrepresented detector unit as described above.

Figure 3:
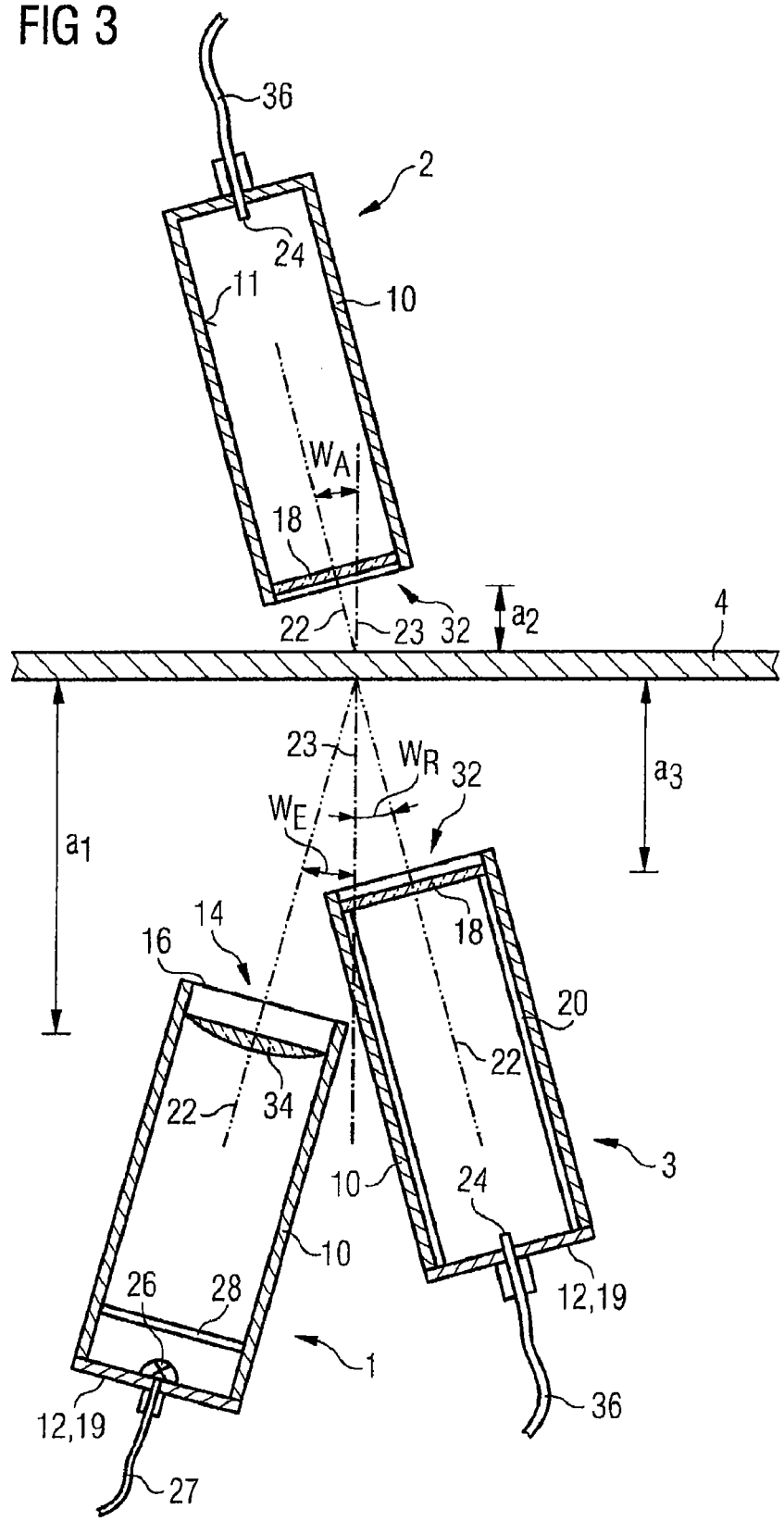

FIG. 3 represents a measuring device with a light transmitter 1 and a light receiver 2 for the measurement of transmission and another light receiver 3 for the measurement of reflection. To this effect, the distance between light transmitter 1 and the substrate 4 is selected in such a manner and arranged against the light transmitter 1 with such an angle of incidence $W_E$ that it is possible to arrange another light receiver 3 in the optical path of light emitted from light transmitter 1 and reflected from the substrate 4 under the angle of angle of reflection $W_R$. For measuring reflection as well, standard geometry can be implemented favorably because of the above-mentioned limitations of the angle of incidence $W_E$ to maximum ±15° likewise CIE diffuse/8°. To this effect, the light transmitter 1 with an angle of incidence of near 8° as well as the other light receiver 3 mirrored on the surface normal 23 are aligned with a comparable angle (angle of reflection $W_R$) different from the angle of incidence $W_E$, so that the other light receiver 3 is still arranged in the optical path of the light reflected from the substrate 4.

Even if the light transmitter 1 emits diffusely dispersed light, it is possible to measure the reflection on account of the mace-like intensity distribution of the emitted light described above. To this effect there are light transmitter 1 and the other light receiver 3 with an angle of incidence $W_E$, the value of which is once again less than 15° and an angle of reflection $W_R$ aligned on the substrate, whereupon both the angles almost correspond to each other. As represented in the execution example, the other light receiver 3 comprises a hollow cylinder with the entrance of a fiber-optic light guide 36 as a light sensor 24. The light sensor 24 is centrally arranged in the base plate 19 of the hollow cylinder 10 facing the light entrance opening 32. A dispersion plate 18 is inserted in the hollow cylinder 10 at the light entrance opening 32, as the dispersive properties of the substrate 4 do not work while measuring reflection. In this manner, the characteristic intensity distribution in the light receiver, described above can also be obtained for reflection and a reproduction of a light reflex directly on the light sensor 24 can be avoided.

Figure 4:
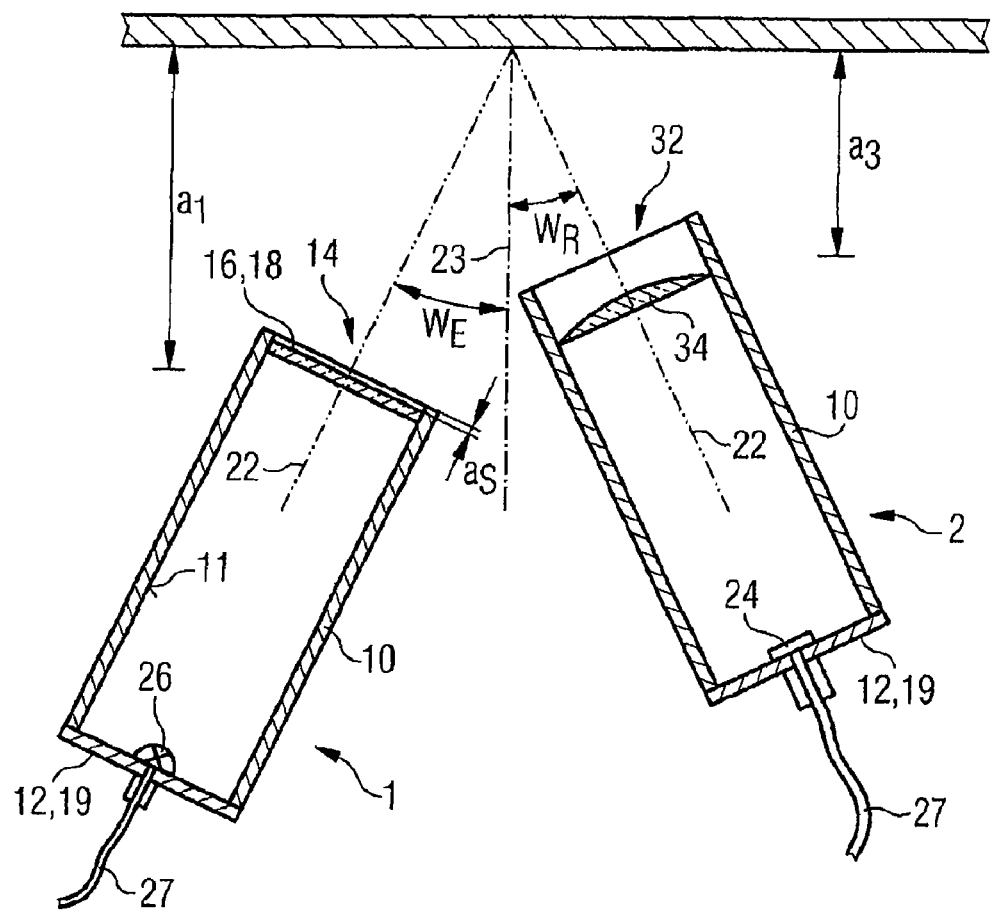

As demonstrated above for the measurement of transmission, the characteristic intensity distribution of light also allows the light exit angle $W_A$ and the angle of reflection in the measuring device for measuring reflection $W_R$ to deviate from each other slightly i.e. in the minimum degree range according to FIG. 4. The extent of the possible difference between the two angles also depends on different measurement parameters e.g. geometric parameters such as the diameter of the light exit opening 14 and the light entrance opening 32, the distance between the light transmitter 1 or light receiver 2 and the substrate 4 or on the wave length and intensity of the light emitted from the light source 26, the reflectivity of the substrate 4 and other parameters.

There are no other requirements from the light transmitter 1 other than the emission of collimated light on the substrate 4. To this effect, similar to the light transmitter in FIG. 2, a hollow cylinder 10 with a single light source 26 is used, here a halogen lamp in its base plate 19 and a collimator 34 close to the light exit opening 14. A blue filter 28 is inserted in the hollow cylinder 10 near the light source 26 in order to balance the yellowish spectrum of the halogen lamp. Even here, another suitable light transmitter 1 can be used as an alternative to the one described which meets the requirements of the light to be emitted.

In this embodiment of the measuring device, the light transmitter 2 for measuring transmission complies with the light receiver in FIG. 1 in design, function and arrangement, so that the above demonstrations are referred to for this purpose. It is only by way of example that a dispersion plate 18 is inserted in the hollow cylinder 10 of the light receiver 2.

Another embodiment (FIG. 4) of the measuring device serves only for measuring the reflection of the substrate 4. A light transmitter 1 with a hollow cylinder 10 with diffusely dispersive inner surfaces 11 and a dispersion plate 18 at the light exit opening 14 aligns diffusely dispersed light on a substrate 4. A light receiver 2, the basic design of which complies with that in FIG. 1 is arranged as a mirror image of the light transmitter 1, with the surface normal 23 of the substrate 4 as the axis of reflection. The light incident through the light exit opening 32 with different directions of propagation is arranged parallel by means of a collimator 34 and is incident on the light sensor 24, e.g. a photodiode, which is bound to a cable 27 with an unrepresented unit of evaluation. Here, the light sensor 24 is in the base plate 19 of the light receiver and is thus arranged facing the light entrance opening 32.

In the described embodiment of the measuring device, light transmitters and light receivers according to the invention have been described in different combinations with conventional light transmitters and light receivers for different applications. These embodiments merely represent possible examples with respect to the design, combination and application and in no way a final enumeration. Other useful modifications that can be carried out by the expert within the scope of the content of the invention are obviously possible and included herewith.

The invention claimed is:

1. Measuring device for measuring optical properties of a transparent substrate, comprising:
   a light transmitter arranged relative to a surface of the substrate facing the light transmitter with a defined angle of incidence between an optical axis of the light transmitter and a surface normal of the substrate and emitting diffuse light for illuminating the substrate; and
   at least one light receiver arranged in an optical path of light emitted from the light transmitter and passing through the substrate with an emergent angle between an optical axis of the light receiver and the surface normal of the substrate;
   wherein:
   a) the light transmitter comprises a hollow cylinder with a highly reflective, diffusely dispersive cylindrical inner surface, a first light source arranged in an interior of the hollow cylinder, and a light exit opening arranged in a first base of the hollow cylinder at a distance from the light source, and the light source is arranged at such a distance from the light exit opening and with such direction of propagation of light that light emitted from the light source and multiply reflected in the hollow cylinder emerges as diffuse light from the light exit opening; and/or
   b) the light receiver comprises a hollow cylinder with a highly reflective, diffusely dispersive cylindrical inner surface, a light sensor arranged in an interior of the hollow cylinder, and a light entrance opening arranged in a first base of the hollow cylinder at a distance from the light sensor, and the light sensor is arranged at such a distance from the light entrance opening and with such a direction of incidence of the light that light entering the light entrance opening and multiply reflected in the hollow cylinder emerges on the light sensor as diffuse light;

and wherein the angle of incidence is not equal to the emergent angle.

2. Measuring device for measuring optical properties of a transparent substrate, comprising:

a light transmitter arranged relative to a surface of the substrate facing the light transmitter with a defined angle of incidence between an optical axis of the light transmitter and a surface normal of the substrate and emitting diffuse light for illuminating the substrate; and at least one light receiver arranged in an optical path of light emitted from the light transmitter and reflected from the substrate with an angle of reflection between an optical axis of the light receiver and the surface normal of the substrate;

wherein:

a) the light transmitter comprises a hollow cylinder with a highly reflective, diffusely dispersive cylindrical inner surface, a first light source arranged in an interior of the hollow cylinder, and a light exit opening arranged in a first base of the hollow cylinder at a distance from the light source, and the light source is arranged at such a distance from the light exit opening and with such direction of propagation of light that light emitted from the light source and multiply reflected in the hollow cylinder emerges as diffuse light from the light exit opening; and/or b) the light receiver comprises a hollow cylinder with a highly reflective, diffusely dispersive cylindrical inner surface, a light sensor arranged in an interior of the hollow cylinder, and a light entrance opening arranged in a first base of the hollow cylinder at a distance from the light sensor, and the light sensor is arranged at such a distance from the light entrance opening and with such a direction of incidence of the light that light entering the light entrance opening and multiply reflected in the hollow cylinder emerges on the light sensor as diffuse light;

and whereupon the angle of incidence is not equal to the angle of reflection.

3. Measuring device according to one of claims 1 or 2, wherein the light transmitter is arranged at a distance from the substrate.

4. Measuring device according to one of claims 1 or 2, wherein the angle of incidence falls in the range of 0° to ±15°.

5. Measuring device according to claim 4, wherein the angle of incidence falls in the range of 0° to ±10°.

6. Measuring device according to claim 1, wherein the emergent angle is greater than 0°.

7. Measuring device according to claim 6, wherein the emergent angle is close to 8°.

8. Measuring device according to one of claims 1 or 2, wherein the light exit opening and/or the light entrance opening is fully covered with a first light diffusion disk.

9. Measuring device according to claim 8, further comprising a second light diffusion disk arranged in the hollow cylinder in parallel and spaced from the first disk such that the light emerging through the light exit opening and/or entering through the light entrance opening passes through the second diffusion disk.

10. Measuring device according to claim 9, wherein at least one diffusion disk comprises a holographic diffuser.

11. Measuring device according to claim 9, wherein at least one diffusion disk comprises an even, sandblasted glass or plastic disk.

12. Measuring device according to one of claims 1 or 2, wherein the light exit opening and/or the light entrance opening exhibits dimensions of the first base.

13. Measuring device according to claim 9, wherein the second diffusion disk exhibits dimensions of the first base.

14. Measuring device according to one of claims 1 or 2, wherein the light source and/or the light sensor are arranged in a second base located opposite the first base.

15. Measuring device according to one of claims 1 or 2, further comprising at least one filter arranged in the hollow cylinder in the optical path of light.

16. Measuring device according to one of claims 1 or 2, wherein the light source comprises an exit and/or the light sensor comprises an entry of a fiber-optic light guide.

17. Measuring device according to one of claims 1 or 2, wherein the inner surface of the hollow cylinder is formed by at least one inner hollow cylinder that can be retracted in an outer cylinder.

18. Measuring device according to claim 17, where upon the inner hollow cylinder comprises two inner hollow cylindrical sections and a diffusion disk and/or a disk-shaped filter between the two inner hollow cylindrical sections.

19. Measuring device according to one of claims 1 or 2, further comprising a second, operable light source independent of the first light source arranged in the hollow cylinder in such a manner that light emitted in the hollow cylinder from the second light source as well is multiply reflected and emerges from the light exit opening as diffuse light.

20. Measuring device according to claim 19, wherein at least one light source emits monochromatic light.

21. Measuring device according to claim 19, wherein at least one light source emits polychromatic light.

22. Measuring device according to one of claims 1 or 2, wherein the light sensor comprises an entrance of a fiber-optic light guide with a collimator.

23. Measuring device according to one of claims 1 or 2, wherein the light sensor comprises a laminar arrangement of several sensor elements.

* * * * *